United States Patent [19]

McGredy, IV

[11] Patent Number: Plant 7,202

[45] Date of Patent: Mar. 27, 1990

[54] ROSE PLANT NAMED MAC COMPU

[75] Inventor: Sam McGredy, IV, Auckland, New Zealand

[73] Assignee: Co-Operative Rose Growers, Inc., Tyler, Tex.

[21] Appl. No.: 337,462

[22] Filed: Apr. 13, 1989

[51] Int. Cl.[4] ..... A01H 5/00

[52] U.S. Cl. ..... Plt./16

[58] Field of Search ..... Plt. 16

*Primary Examiner*—James R. Feyrer

*Attorney, Agent, or Firm*—Christie, Parker & Hale

[57] ABSTRACT

A new and unusual bright orange and yellow bicolor Grandiflora rose.

1 Drawing Sheet

SUMMARY OF THE INVENTION

The present invention relates to a new and distinct variety of rose plant of the Grandiflora rose class, which was originated by my crossing as seed parent and as pollen parent two unnamed, unpatented seedlings of my creation. The varietal denomination of this new rose is "Mac Compu".

Among the novel characteristics possessed by this new variety which distinguish it from its parents and all other varieties of which I am aware are its unusual bright orange and yellow bicolored flowers in this class of rose. Flowers are long lasting on the plant and after cutting. Asexual reproduction by budding of the new variety as performed in Smith County, Tex., shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development depicted in color as nearly true as it is reasonably possible to make the same in a color illustration of this character.

DESCRIPTION OF PREFERRED EMBODIMENT

The following is a detailed description of my new variety, with color terminology in accordance with the Royal Horticultural Society Colour Chart (RHSCC). The terminology used in color description herein refers to plate numbers in the aforementioned color chart, e.g., "28A" is plate 28A of the Royal Horticultural Society Colour Chart.

Parentage: Seedling.

*Seed parent.*—Unnamed seedling.

*Pollen parent.*—Unnamed seedling.

Class: Grandiflora.

The following observations are made of specimens grown outdoors in Smith County, Tex., during the month of October.

FLOWER

Blooming habit: Nearly continuous.

A. Bud:

(1) *Size.*—Medium.

(2) *Form.*—Urn shaped.

(3) *Color.*—As sepals divide, bud color is near 28A mixed with near 15B.

(4) *Sepals.*—Longer than bud, foliated.

(5) *Peduncle.*—Length — average. Aspect — straight. Strength — erect. Color — near 144B.

B. Bloom:

(1) *Size.*—Average size when fully expanded — about 3½-inches.

(2) *Borne.*—Singly, one to a stem and in sprays of three to five blooms.

(3) *Form.*—High centered at first, becoming flat. Outer petals reflex and quill to points; inner petals roll under.

(4) *Petalage.*—Number of petals under normal conditions — about 35.

(5) *Color.*—After sepals fall and petals unfurl, predominant flower color viewing petals' top surface is near 28A to 21D with flowers varying in color through this range producing an overall bright orange color effect. Flowers exhibit deeper toned orange suffusion more pronounced in outer petals which are deeper toned than inner petals. Petal under-surface tends toward near 13B suffused with near 28B. Color at point of petal attachment is near 15C. Overall tonality from a distance is bright orange, near 25A to 28A. Color changes as blooms age to near 25A to 28B.

C. Petals:

(1) *Texture.*—Thick.

(2) *Appearance.*—Inside velvety and outside satiny.

(3) *Form.*—Broad, fan shaped with pointed apices.

(4) *Arrangement.*—Regularly arranged, imbricated.

(5) *Petaloids in center.*—Few.

(6) *Persistence.*—Average.

(7) *Fragrance.*—Slight.

(8) *Lasting quality.*—Average.

REPRODUCTIVE ORGANS

A. Stamens, filaments and anthers:

(1) *Arrangement.*—Regularly arranged around styles.

(2) *Color.*—Filaments yellow.

B. Pollen:

*Color.*—Yellow.

C. Styles: Even, medium length.

D. Stigmas:

*Color.*—Ivory.

E. Hips: Globular, average size, orange red color, seeds sometimes protrude.

PLANT

A. Form: Spreading.

B. Growth: Average vigor.

*Height attained.*—About 3½ feet to 4 feet.

C. Foliage: Compound 5 leaflets.

(1) *Size.*—Medium.

(2) *Quantity.*—Abundant.

(3) *Color.*—New foliage: Upper side — near 144A. Under side — near 182B. Old foliage: Upper side — near 141B. Under side — near to 138B.

(4) *Shape.*—Oval, pointed.

(5) *Texture.*—Upper side is glossy and under side is matte.

(6) *Edge.*—Serrate.

(7) *Serration.*—Ordinary.

(8) *Leaf stem.*—Color — near to 145B. Under side — near 150C.

(9) *Stipules.*—Medium length.

(10) *Resistance to disease.*—Blackspot — Average. Mildew — Good.

D. Wood:

(1) *New wood.*—Color — purplish green. Bark — smooth.

(2) *Old wood.*—Color — dark green. Bark — smooth.

E. Thorns:

(1) *Thorns.*—Quantity (main stalk) — ordinary. On laterals from stalk — few. Form — flat base. Length — medium. Color — purplish.

F. Winter hardiness: Needs protection in severe climates.

I claim:

1. A new and distinct variety of rose plant of the Grandiflora rose class, substantially as shown and described, characterized particularly by attractive bright orange flowers.

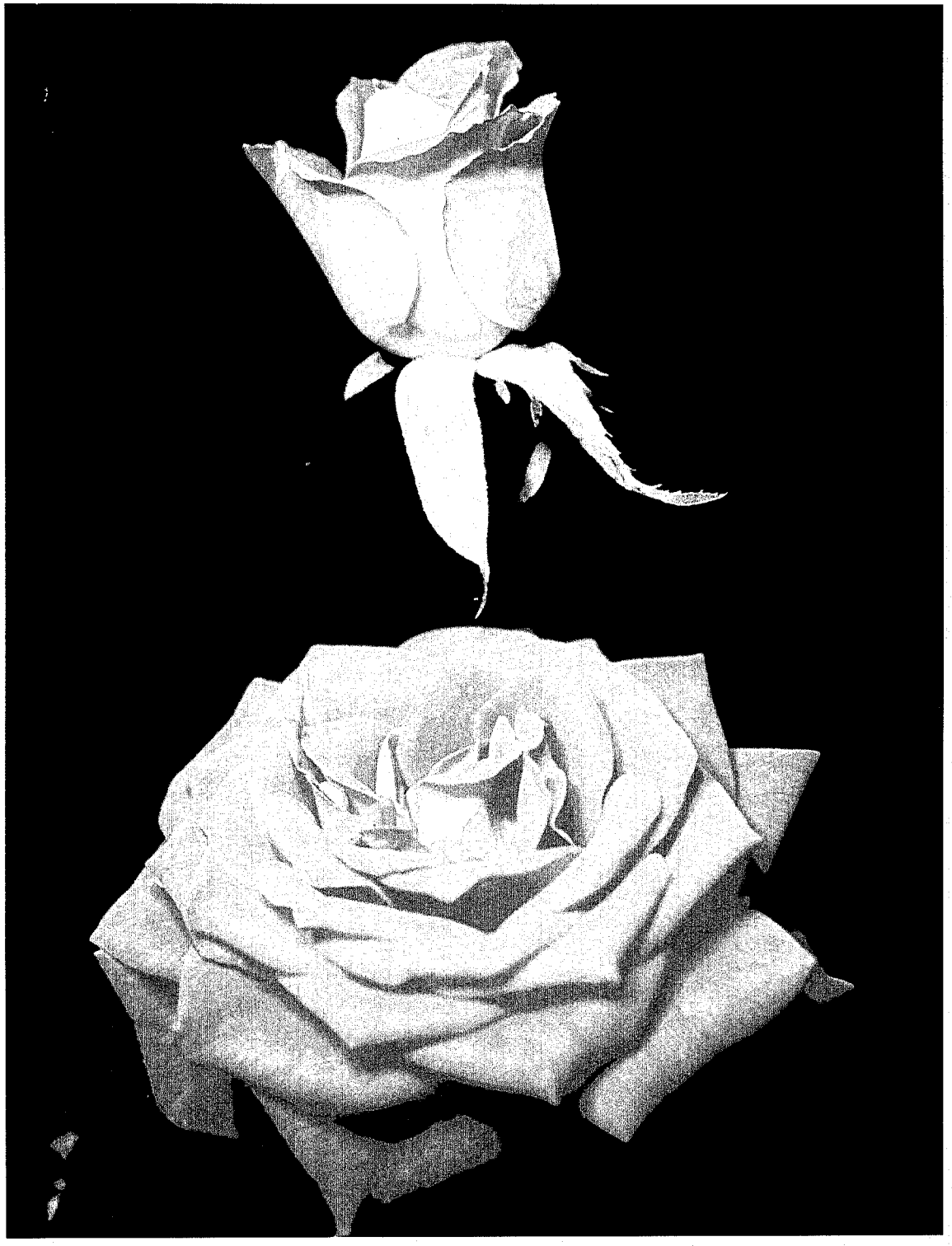

* * * * *